United States Patent
Zhao

(10) Patent No.: US 12,134,781 B2
(45) Date of Patent: *Nov. 5, 2024

(54) ELECTROPHORESIS DEVICE

(71) Applicant: Memphasys Limited, Homebush West (AU)

(72) Inventor: Xing Feng Zhao, North Rocks (AU)

(73) Assignee: Memphasys Limited, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/894,975

(22) Filed: Aug. 24, 2022

(65) Prior Publication Data

US 2023/0127490 A1  Apr. 27, 2023

Related U.S. Application Data

(63) Continuation of application No. 16/343,676, filed as application No. PCT/AU2017/051136 on Oct. 20, 2017, now Pat. No. 11,466,250.

(30) Foreign Application Priority Data

Oct. 20, 2016 (AU) ................. 2016904260

(51) Int. Cl.
*C12N 5/00* (2006.01)
*B01D 57/02* (2006.01)
(Continued)

(52) U.S. Cl.
CPC .......... *C12N 5/0612* (2013.01); *B01D 57/02* (2013.01); *B01D 63/08* (2013.01); *B01D 69/02* (2013.01);
(Continued)

(58) Field of Classification Search
CPC ...... C12N 5/0644; C12N 5/0608–0612; G01N 1/4005; G01N 2001/4011;
(Continued)

(56) References Cited

U.S. PATENT DOCUMENTS 4,415,418 A * 11/1983 Turre ............... G01N 27/44756
204/616
4,673,483 A * 6/1987 Mandle ................ B01D 57/02
204/627

(Continued)

FOREIGN PATENT DOCUMENTS

AU      2004238088 B2    11/2004
WO   WO-2000/071999 A1   11/2000
(Continued)

OTHER PUBLICATIONS

Fleming et al., "Prospective controlled trial of an electrophoretic method of sperm preparation for assisted reproduction: comparison with density gradient centrifugation," Human Reproduction vol. 23, No. 12 pp. 2646-2651, 2008 (Year: 2008).*

(Continued)

*Primary Examiner* — Alexander S Noguerola
(74) *Attorney, Agent, or Firm* — Morse, Barnes-Brown & Pendleton, P.C.; Stanley F. Chalvire, Esq.

(57) ABSTRACT

The present invention relates to apparatuses for use in electrophoretic separation of macromolecules and/or cells.

11 Claims, 9 Drawing Sheets

(51) Int. Cl.
*B01D 63/08* (2006.01)
*B01D 69/02* (2006.01)
*B01D 71/38* (2006.01)
*B01D 71/50* (2006.01)
*C12N 5/071* (2010.01)
*C12N 5/076* (2010.01)
*C12N 5/078* (2010.01)
*G01N 27/447* (2006.01)
*G01N 27/453* (2006.01)

(52) U.S. Cl.
CPC ............. *B01D 71/38* (2013.01); *B01D 71/50* (2013.01); *C12N 5/00* (2013.01); *C12N 5/0081* (2013.01); *C12N 5/061* (2013.01); *C12N 5/0644* (2013.01); *G01N 27/44704* (2013.01); *G01N 27/44756* (2013.01); *B01D 2313/44* (2013.01); *B01D 2319/06* (2013.01); *C12N 2529/00* (2013.01)

(58) Field of Classification Search
CPC ... G01N 2001/4016; G01N 2001/4038; G01N 27/447; G01N 27/44704; G01N 27/44791; G01N 27/453; B01D 57/02; B01D 2313/44; B01D 61/42; B01D 61/422; B01D 61/44; B01D 61/46; B01D 63/08; B01D 63/082; B01D 63/088
See application file for complete search history.

(56) References Cited

U.S. PATENT DOCUMENTS

| | | | | |
|---|---|---|---|---|
| 5,854,217 A | * | 12/1998 | Maccecchini | C07K 14/435 514/17.7 |
| 6,261,431 B1 | | 7/2001 | Mathies et al. | |
| 6,969,453 B2 | | 11/2005 | Ogle et al. | |
| 7,198,703 B2 | * | 4/2007 | Rooney | G01N 27/44704 204/606 |
| 8,088,265 B2 | | 1/2012 | Rylatt et al. | |
| 11,466,250 B2 | * | 10/2022 | Zhao | C12N 5/0644 |
| 2002/0043465 A1 | | 4/2002 | Vigh et al. | |
| 2003/0000836 A1 | | 1/2003 | Wang et al. | |
| 2003/0187380 A1 | | 10/2003 | Botto et al. | |
| 2008/0067070 A1 | | 3/2008 | Rylatt et al. | |
| 2009/0101507 A1 | | 4/2009 | Aitken et al. | |
| 2015/0037864 A1 | * | 2/2015 | James | C12N 13/00 435/173.9 |

FOREIGN PATENT DOCUMENTS

| | | | |
|---|---|---|---|
| WO | WO-2001/036449 A1 | 5/2001 | |
| WO | WO-2001/078878 A1 | 10/2001 | |
| WO | WO-2004/101117 A1 | 11/2004 | |
| WO | WO 2005033295 A1 * | 4/2005 | ............... C12N 5/00 |
| WO | WO-2013/136091 A1 | 9/2013 | |
| WO | WO-2013/186567 A1 | 12/2013 | |
| WO | WO-2017/181240 A1 | 10/2017 | |

OTHER PUBLICATIONS

Trizma® Sigma-Aldrich product description, downloaded Dec. 30, 2020 (Year: 2020).*

Cambridge University online dictionary definition of "preferably" downloaded Mar. 7, 2024 from https://dictionary.cambridge.org/us/dictionary/english/preferably.*

Fleming, et al., "Prospective controlled trial of an electrophoretic method of sperm preparation for assisted reproduction: comparison with density gradient centrifugation," *Human Reproduction*, 23:12, Dec. 2008, pp. 2646-2651.

Fleming, et al., "Electrophoretic Sperm Separation," *Sperm Chromatin: Biological and Clinical Applications in Male Infertility and Assisted Reproduction* (2011).

Trizma® Sigma-Aldrich product description downloaded Dec. 30, 2020 from https://www.sigmaaldrich.com/life-science/core-bioreagents/biological-buffers/trizma-specification.printerview.html.

Ainsworth, et al., "Development of a novel electrophoretic system for the isolation of human spermatozoa," *human reproduction*, 20:8, Aug. 2005, pp. 2261-2270.

International Search Report issued in International Application No. PCT/AU2017/051136, dated Dec. 8, 2017.

* cited by examiner

ELECTROPHORESIS DEVICE

This present application is a continuation of application Ser. No. 16/343,676, filed Apr. 19, 2019, which is a national stage filing under 35 U.S.C. 371 of International Application No. PCT/AU2017/051136, filed Oct. 20, 2017, which claims priority from Australian Provisional Application No. 2016904260, filed Oct. 20, 2016, the contents of which are incorporated in their entirety herein. International Application No. PCT/AU2017/051136 was published under PCT Article 21(2) in English.

FIELD OF THE INVENTION

The present invention relates to the electrophoretic separation of macromolecules and/or cells. In particular, the present invention relates to apparatuses for use in electrophoretic separation of macromolecules and/or cells.

BACKGROUND OF THE INVENTION

Any discussion of the prior art throughout the specification should in no way be considered as an admission that such prior art is widely known or forms part of common general knowledge in the field.

Electrophoresis is the motion of dispersed particles relative to a fluid under the influence of a spatially uniform electric field. The motion of the dispersed particles is a function of the electrical charge on the particles and the applied field gradient. The combination of electrophoresis with a porous membrane, which allows the passage of charged macromolecules or cells of particular sizes, enables the separation and purification of macromolecules or cells.

Apparatuses suitable for electrophoretic separation of macromolecules or cells are described in WO 2000/013776 and WO 2002/024314. Briefly, a size-exclusion porous membrane (hereinafter referred to as a separation membrane) acts to separate two streams of liquid carrying macromolecules or cells, referred to as the sample stream and the harvest stream. The streams pass on either side of the separation membrane and between charged electrodes. Charged macromolecules or cells that are smaller than the pores in the separation membrane migrate across the membrane from the sample stream to the harvest stream under the influence of the electric field. The apparatus also includes buffer streams and non-water permeable membranes that allow the passage of ions but not macromolecules or cells (hereinafter referred to as restriction membranes) that are disposed between the electrodes and the separation membrane. The sample, harvest and buffer streams are circulated by means of pumps and reservoirs. Circulating buffers (and associated tubing, pumps and reservoirs) are required to avoid the build-up of gasses at the electrodes and increases in temperature and pH during electrolysis. However, as a result of using circulating buffers, the apparatuses described in WO 2000/013776 and WO 2002/024314 are complex and expensive, and difficult to decontaminate. Additionally, the apparatuses employ polyacrylamide (PAm) restriction membranes, which may contaminate the macromolecules or cells due the possible presence of toxic acrylamide monomer in the membranes.

Accordingly, there is a need for an improved apparatus for use in the electrophoretic separation of macromolecules and/or cells.

It is an object of the present invention to overcome or ameliorate at least one of the disadvantages of the prior art, or to provide a useful alternative.

SUMMARY OF THE INVENTION

Previous electrophoresis apparatuses for separation of macromolecules and/or cells in a solution have required the use of circulating buffer streams to prevent:
 (a) build-up of gasses at the electrodes during electrolysis;
 (b) build-up of a pH gradient across the cartridge due to ionic migration to the electrodes; and
 (c) temperature increases in the sample and harvest chambers due to the heating effect of the current.

The present invention is based on the present finding (disclosed for the first time herein) that circulating buffer streams are not required for the electrophoretic separation of macromolecules and/or cells.

In one aspect, the present invention relates to an electrophoresis apparatus for separation of macromolecules and/or cells in a solution, the apparatus comprising:
 a sample chamber and a harvest chamber separated by a size-exclusion membrane (separation membrane);
 buffer chambers flanking each respective sample chamber and harvest chamber, wherein each buffer chamber is separated from each respective sample chamber and harvest chamber by an ion-permeable membrane (restriction membrane); and
 an electrode positioned in each buffer chamber.

In one embodiment, the buffer chambers are non-circulating buffer chambers.

In one embodiment, the buffer chambers are sealed and contain a buffer solution.

In one embodiment, the buffer solution has low electrolyte content.

In one embodiment, the buffer solution does not contain a salt.

In one embodiment, the buffer solution comprises sucrose.

In one embodiment, the buffer solution has a pH of about 7.5 to about 8.5.

In one embodiment, the buffer is a HEPES buffer.

In one embodiment, the buffer is HEPES buffer and comprises sucrose.

In one embodiment, the buffer is HEPES buffer, comprises sucrose and has a pH of about 7.5 to about 8.5.

In one embodiment, the buffer solution contains 30 mM HEPES and 250 mM sucrose, and is adjusted to a pH of 8.2 with Trizma base.

In another aspect, the present invention relates to an electrophoresis apparatus for separation of macromolecules and/or cells in a solution, the apparatus comprising:
 a sample chamber flanked by first and second harvest chambers, each harvest chamber separated from the sample chamber by a size-exclusion membrane (separation membrane);
 buffer chambers flanking each harvest chamber, wherein each buffer chamber is separated from each respective harvest chamber by an ion-permeable membrane (restriction membrane); and
 an electrode positioned in each buffer chamber In one embodiment, each harvest chamber comprises one or more separation membranes, wherein the one or more separation membranes are substantially parallel to the restriction membranes.

In one embodiment, each harvest chamber comprises one or more separation membranes, wherein the one or more separation membranes are substantially parallel to the restriction membranes and wherein the pore size of each of the one or more separation membranes is smaller than the pore size of any separation membrane positioned between it and the sample chamber.

In one embodiment, each sample chamber and harvest chamber contains one or more apertures for adding or removing a solution.

In one embodiment, the apertures may be sealable.

In one embodiment, each sample chamber and harvest chamber contains an inlet and an outlet for circulating a solution through each sample chamber and harvest chambers.

The inlet and outlet may be sealable.

In one embodiment, the apparatus further comprises means for connecting the electrodes to a power source.

In one embodiment, the apparatus is a cartridge that is insertable into a receiving device comprising a power source such that a voltage may be applied to the electrodes.

In one embodiment, the apparatus is a cartridge that is insertable into a receiving device comprising a power source, pumps and reservoirs such that a voltage may be applied to the electrodes and such that the pumps and reservoirs are in fluid communication with each sample chamber and harvest chambers to circulate solutions through each sample chamber and harvest chambers.

In one embodiment, the cartridge is sterile.

In one embodiment, the cartridge is disposable.

In one embodiment, the restriction membranes comprise PVA.

In one embodiment, the sample and harvest chambers are able to be temperature controlled.

In one embodiment, the restriction membranes do not contain PAm.

In one embodiment, the restriction membranes have a molecular weight cut off (MWCO) of less than 15 kDa.

In one embodiment, the restriction membranes have a MWCO of less than 5 kDa.

In one embodiment, the restriction membranes allow passage of an electrical field, but does not allow passage of macromolecules or cells.

In one embodiment, the separation membranes comprise PVA.

In one embodiment, the separation membranes comprise polycarbonate.

In one embodiment, the separation membranes do not contain PAm.

In one embodiment, the pore size of a separation membrane may be about 0.1 μm to about 100 μm.

In one embodiment, the pore size of a separation membrane may be about 0.5 μm to about 30 μm.

In one embodiment, the pore size of a separation membrane may be about 1 μm to about 8 μm.

In one embodiment, the pore size of a separation membrane may be about 1 μm to about 5 μm.

In one embodiment, the pore size of a separation membrane may be about 3 μm to about 5 μm.

In one embodiment, the pore size of a separation membrane may be less than 100 μm.

In one embodiment, the pore size of a separation membrane may be less than 30 μm.

In one embodiment, the pore size of a separation membrane may be less than 10 μm.

In one embodiment, the pore size of a separation membrane may be less than 8 μm.

In one embodiment, the pore size of a separation membrane may be less than 5 μm.

In one embodiment, the pore size of a separation membrane may be less than 1 μm.

In one embodiment, the pore size of a separation membrane may be about 100 μm, about 90 μm, about 80 μm, about 70 μm, about 60 μm, about 50 μm, about 40 μm, about 30 μm, about 20 μm, about 10 μm, about 9 μm, about 8 μm, about 7 μm, about 6 μm, about 5 μm, about 4 μm, about 3 μm, about 2 μm, about 1 μm, about 0.9 μm, about 0.8 μm, about 0.7, about 0.6 μm, about 0.5 μm, about 0.4 μm, about 0.3 μm, about 0.2 μm or about 0.1 μm.

In a further aspect, the present invention relates to the use of the apparatus of the invention for the separation of sperm.

In a further aspect, the present invention relates to the use of the apparatus of the invention for the separation of cells.

In a further aspect, the present invention relates to the use of the apparatus of the invention for the separation of macromolecules.

In a further aspect, the present invention relates to the use of the apparatus of the invention for the separation of sperm.

In a further aspect, the present invention relates to the use of the apparatus of the invention for the separation of platelets.

In a further aspect, the present invention relates to a method of separation of macromolecules and/or cells in a solution, the method comprising adding a sample containing macromolecules and/or cells to the sample chamber of the apparatus of the invention, applying a voltage to the electrodes and collecting separated macromolecules and/or cells from the harvest chamber(s).

In the context of the present invention, the words "comprise", "comprising" and the like are to be construed in their inclusive, as opposed to their exclusive, sense, that is in the sense of "including, but not limited to".

As used herein, the term "restriction membrane" means a membrane that allows passage of an electrical field, but does not allow passage of macromolecules or cells.

As used herein, the term "separation membrane" means a porous size exclusion membrane.

As used herein, the term "PAm" means polyacrylamide.

As used herein, the term "PVA" means poly (vinyl alcohol).

As used herein, the terms "MWO" or "molecular weight cut off" in relation to a membrane refer to the to the lowest molecular weight solute (in daltons) wherein at least 90% of the solute is retained by a membrane, or the approximate molecular weight of a molecule that is 90% retained by a membrane.

As used herein, the term "pore size" in relation to a membrane refers to the diameter of a macromolecule or cell that is retained by the membrane.

As used herein, the term "macromolecule" means a molecule containing a very large number of atoms, commonly created by polymerization of smaller subunits (monomers). Examples of macromolecules include proteins, peptides, nucleic acids and synthetic polymers.

As used herein, the term "cartridge" means a case or container that holds a device or apparatus, and that be easily changed or replaced.

PREFERRED EMBODIMENT OF THE INVENTION

Although the invention has been described with reference to certain embodiments detailed herein, other embodiments can achieve the same or similar results. Variations and modifications of the invention will be obvious to those skilled in the art and the invention is intended to cover all such modifications and equivalents.

The present invention relates to an apparatus for the electrophoretic separation of macromolecules or cells in a solution.

Previous electrophoresis apparatuses for separation of macromolecules and/or cells in a solution have required the use of circulating buffer streams to prevent build-up of gasses at the electrodes and increases in temperature and pH resulting from electrolysis.

The present invention is based on the finding (disclosed for the first time herein) that circulating buffer streams are not required for the electrophoretic separation of macromolecules and/or cells when a buffer of low electrolyte content is used. Such a buffer reduces currents by 90% and, as a result, substantially reduces temperature and pH increases (and variances) across the apparatus during electrophoresis processing. This enables the use of sealed buffer chambers within the apparatus and the elimination of external tubing, pumps and reservoirs for the buffers.

In the electrophoretic separation of macromolecules and/or cells, an electric field applied to a solution will cause positively-charged macromolecules or cells contained within the solution to move to the negative electrode (anode) and negatively-charged macromolecules or cells to move towards the positive electrode (cathode).

In the apparatus of the present invention, a separation membrane is positioned in an electric field and macromolecules and/or cells that are smaller than the pore size of the separation membrane pass through the separation membrane from a sample solution to a harvest solution. The pore size of the separation membrane will vary depending on the size of the macromolecules or cells to be separated.

The sample and harvest solutions are separated from the electrodes by restriction membranes that allow the passage of ions but not macromolecules or cells. The electrodes are in a buffer solution which provides a voltage gradient to be established across the cartridge and for ions to flow and generate an electric current flowing between the electrodes.

The use of sucrose in the buffer solution removes the need to use circulating buffer streams.

The solutions in the sample and harvest chambers may be modified to promote cell survival.

Having outlined some of the principles of operation of the apparatus, the apparatus itself will now be described.

Figure 1:
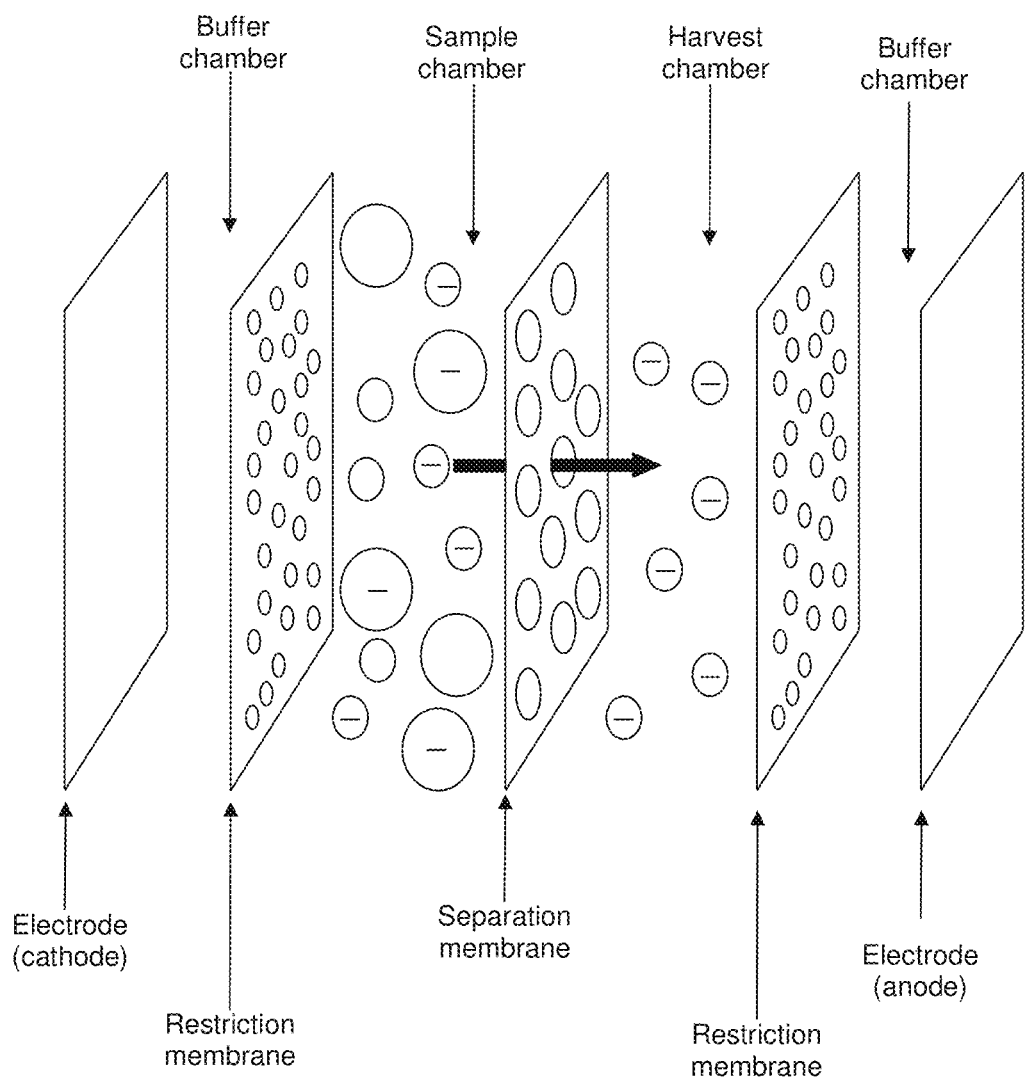
FIG. 1: schematic representation showing the general functionality of the apparatus of the present invention.

Referring to FIG. 1, which is a schematic representation showing the general functionality of the apparatus of the present invention, the apparatus contains a sample chamber and a harvest chamber separated by a separation membrane. The sample and harvest chambers are flanked by buffer chambers, wherein the buffer chambers are separated from the sample and harvest chambers by restriction membranes. A voltage applied to electrodes positioned in the buffer chambers induces an electric field across the separation membrane, resulting in negatively-charged macromolecules or cells in the sample chamber that are smaller than the pore size of the separation membrane moving from the sample chamber into the harvest chamber.

Figure 2:
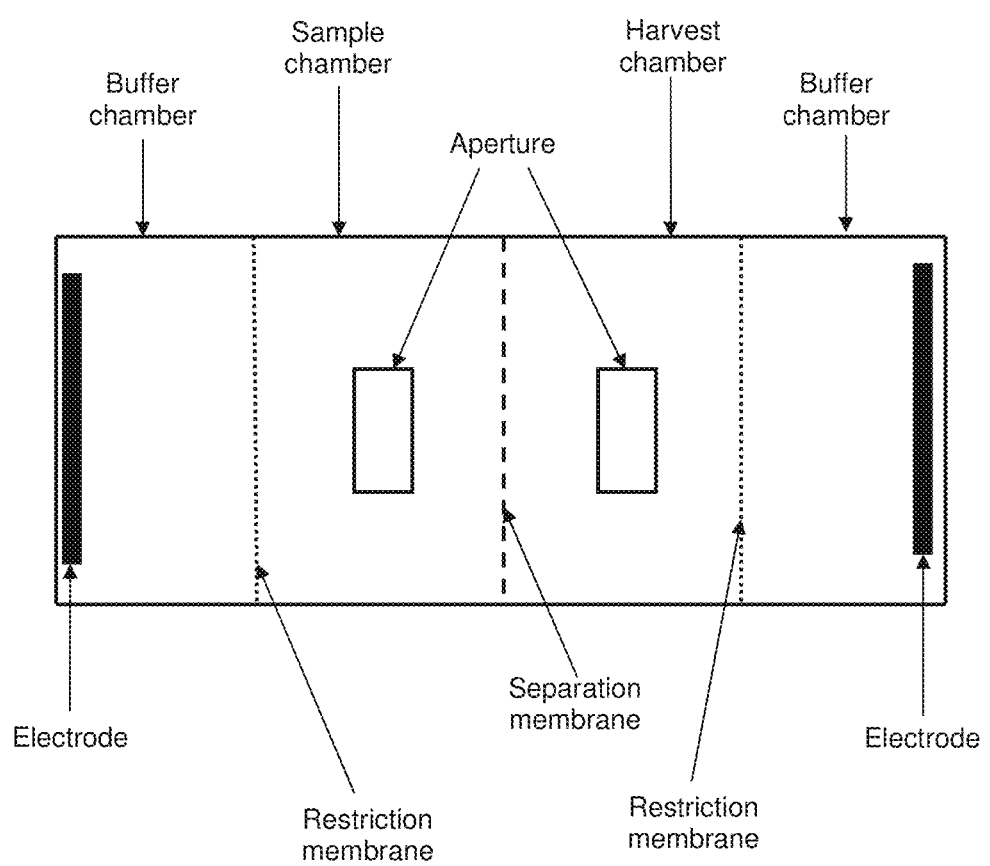
FIG. 2: schematic representation of one embodiment of the apparatus of the present invention.

Referring to FIG. 2, which is a schematic representation of one embodiment of the apparatus of the present invention, the apparatus contains sample and harvest chambers separated by a separation membrane. Buffer chambers containing an electrode flank the sample and harvest chambers. The buffer chambers are separated from the sample and harvest chambers by restriction membranes. The buffer chambers are sealed and contain a buffer solution of low electrolyte content. The sample and harvest chambers contain apertures for adding or removing solutions.

Figure 3:
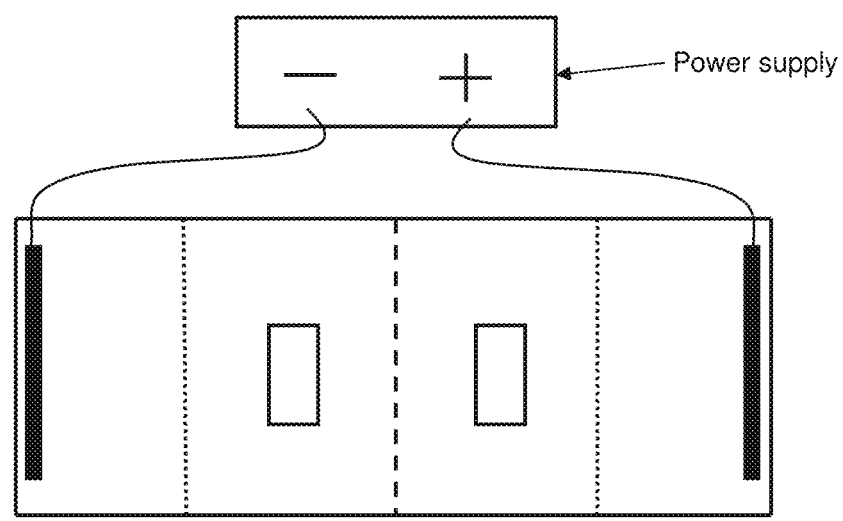
FIG. 3: schematic representation of the apparatus of FIG. 2 in use.

Referring to FIG. 3, which is a schematic representation of the apparatus of FIG. 2 in use, the sample chamber is loaded with a solution containing macromolecules or cells via the respective aperture and the harvest chamber is loaded with a receiving solution via the respective aperture. The electrodes are connected to a power source and a voltage gradient is applied. Negatively-charged macromolecules or cells in the sample chamber migrate towards the anode, with macromolecules or cells smaller than the pore size of the separation membrane passing through the separation membrane and into the harvest chamber. The solution containing the separated macromolecules or cells is extracted from the harvest chamber via the aperture. Should it be desirable to separate positively-charged macromolecules or cells, the connections to the power source may be reversed such that the positively-charged macromolecules or cells pass from the sample chamber into the harvest chamber. Alternatively, a second harvest chamber may be positioned between the sample chamber and the buffer chamber housing the cathode, and separated from the sample chamber by a second separation membrane (FIG. 4).

Figure 5:
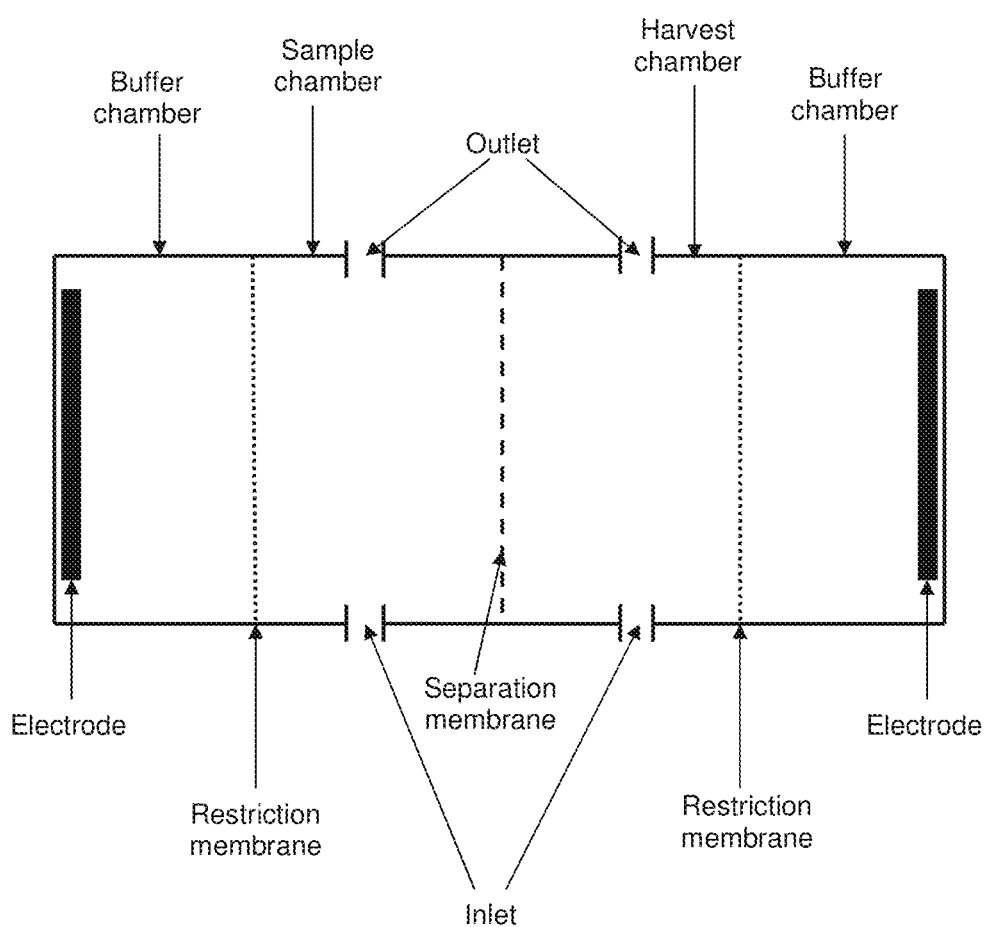
FIG. 5: schematic representation of an alternative embodiment of the apparatus of the present invention.

Referring to FIG. 5, which is a schematic representation of an alternative embodiment of the apparatus of the present invention, the apparatus contains sample and harvest chambers separated by a separation membrane. Two buffer chambers containing an electrode flank the sample and harvest chambers. The buffer chambers are separated from the sample and harvest chambers by restriction membranes. The buffer chambers are sealed and contain a buffer solution of low electrolyte content. The sample and harvest chambers contain an inlet and an outlet for circulating solutions through the sample and harvest chambers.

Figure 4:
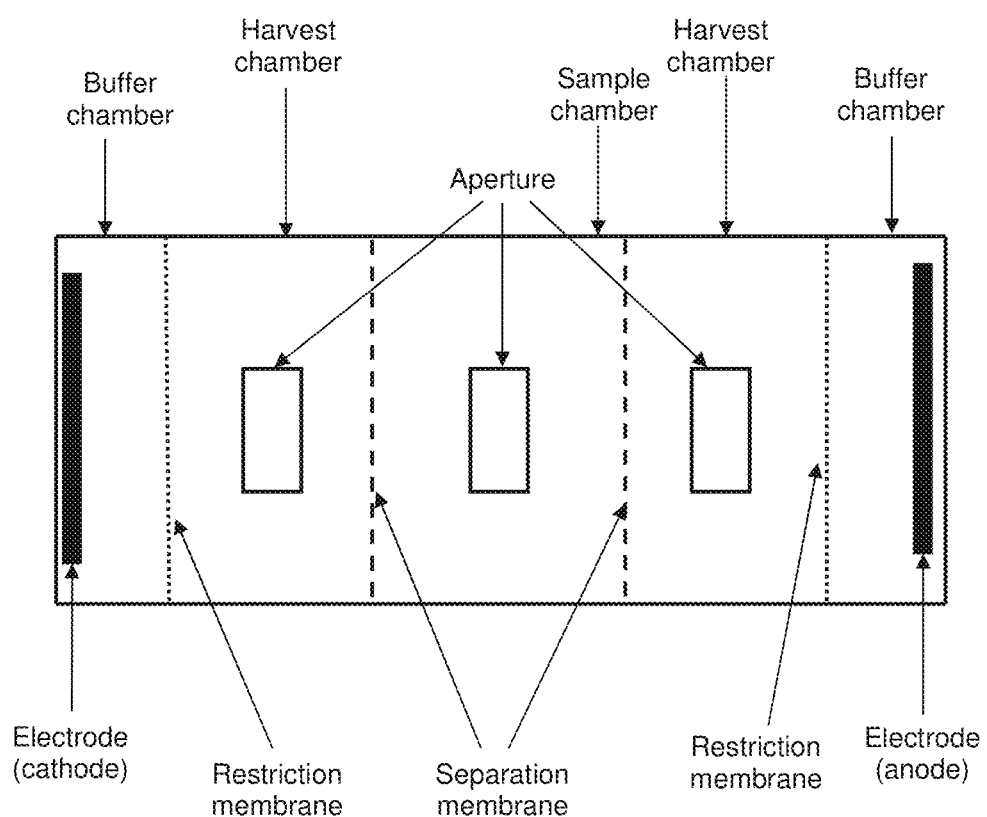
FIG. 4: schematic representation of an alternative embodiment of the apparatus of the present invention.
Figure 6:
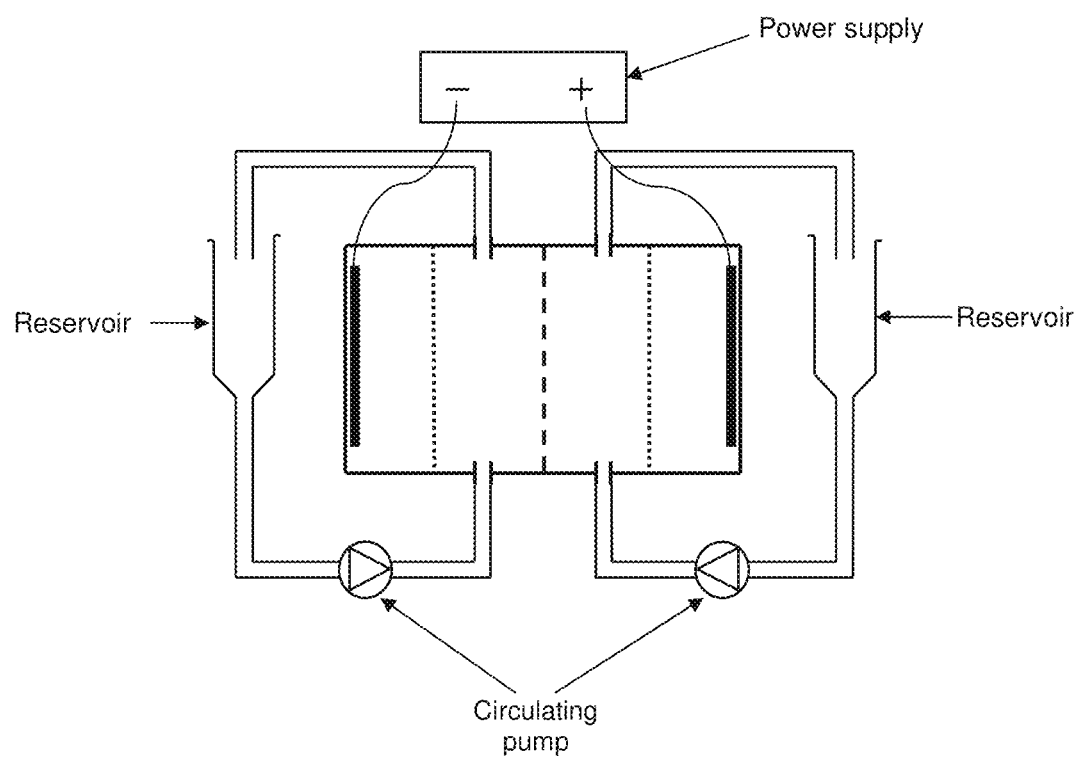
FIG. 6: schematic representation of the apparatus of FIG. 4 in use.

Referring to FIG. 6, which is a schematic representation of the apparatus of FIG. 4 in use, the sample and harvest chambers are connected via their respective inlets and outlets to sample and harvest loops containing reservoirs and circulating pumps to generate sample and harvest streams in the sample and harvest chambers. The reservoir in the sample loop is loaded with a solution containing macromolecules or cells and the reservoir in the harvest loop is loaded with a receiving solution. The electrodes are connected to a power source and a voltage gradient is applied. Negatively-charged macromolecules or cells in the sample stream migrate towards the anode, with macromolecules or cells smaller than the pore size of the separation membrane passing through the separation membrane and into the harvest stream. The separated macromolecules or cells are extracted from the reservoir in the harvest loop. Should it be desirable to separate positively-charged macromolecules or cells, the connections to the power source may be reversed such that the positively-charged macromolecules or cells pass from the sample stream into the harvest stream or a second harvest stream may be positioned between the sample stream and the buffer chamber housing the cathode, and separated from the sample stream by a second separation membrane.

The use of a buffer with low electrolyte content results in a low current and avoids the use of circulating buffers. This creates a still environment for the separation process in the cartridge, compared to a pulsating environment caused by the buffer circulation pump.

The use of sealed buffer chambers allows for the apparatus, including electrodes, to be sterile and/or disposable.

EXAMPLES

Example 1—Separation of Sperm

Performance of the sealed non-circulating buffer cartridge (SNC) of the present invention was compared to an existing electrophoresis device (CS10) in the separation of human sperm (which are particularly sensitive to small changes in temperature and pH).

PVA restriction membranes with a MWCO of 5 kDA and polycarbonate separation membranes with a pore size of 5 μm, were employed in both the CS10 and the SNC.

The CS10 uses circulating electrode buffers containing 30 mM sodium chloride, and a potential difference of 14 volts results in a current of 60-90 mAmps.

The SNC uses sealed electrode chambers containing a buffer with low electrolyte content (30 mM HEPES and 250 mM Sucrose, pH adjusted to 7.8 with Trizma base—referred to as CSM-15 buffer), and a potential difference of 35 volts results in a current of 10 mAmps.

Sperm count was measured by haemocytometer and viability assessed by Eosin-Nigrosin staining.

The results for voltage and current for the CS10 are presented in Table 1.

TABLE 1

| Time point (min) | 0 | 1 | 2 | 3 | 4 | 5 |
|---|---|---|---|---|---|---|
| Voltage (volts) | 14 | 14 | 14 | 14 | 14 | 14 |
| Current (mAmps) | 66 | 66 | 76 | 84 | 88 | 88 |
| Temperature (C. °) | 19.5 | 19.5 | 20.9 | 21.3 | 21.1 | 21.2 |

The results for voltage and current for the SNC are presented in Table 2.

TABLE 2

| Time point (min) | 0 | 1 | 2 | 3 | 4 | 5 |
|---|---|---|---|---|---|---|
| Voltage (volts) | 35 | 35 | 35 | 35 | 35 | 35 |
| Current (mAmps) | 8 | 8 | 10 | 10 | 8 | 8 |
| Temperature (C. °) | 20.2 | 20.3 | 20.6 | 20.5 | 20.8 | 21.1 |

The results for separated sperm for the CS10 are shown in Table 3 (14 volts, 5 minutes).

TABLE 3

| Sample | Sperm conc. ($10^6$/mL) | Total sperm ($10^6$) (conc. × volume in mL) | Harvest rate (%) | Viability (%) | Motility (%) |
|---|---|---|---|---|---|
| Original semen (600 μL) | 62 | 37.2 | 100 | 65 | 51 |
| Residual (R) | 29 | 17.4 | 46.8 | 58 | 40 |
| Selected (S) | 7 | 4.2 | 11.3 | 84 | 65 |
| % recovery ((S + R)/ unprocessed) | | 58% | n/a | n/a | n/a |

"Residual" refers the sperm remaining in the sample chamber after electrophoresis and "Selected" refers to the sperm in the harvest chamber.

The results for separated sperm for the SNC are shown in Table 4 (35 volts, 5 minutes). Briefly, CSM-15 buffer was placed in the sample and harvest chambers and allowed to equilibrate. The buffer in the sample chamber was removed and replaced with a semen sample and a voltage applied to the electrodes.

TABLE 4

| Sample | Sperm conc. ($10^6$/mL) | Total sperm ($10^6$) (conc. × volume in mL) | Harvest rate (%) | Viability (%) | Motility (%) |
|---|---|---|---|---|---|
| Original semen (600uL) | 35 | 21 | 100 | 63 | 43 |
| Residual (R) | 29 | 17.4 | 82.8 | 52 | 41 |
| Selected (S) | 5.2 | 3.12 | 14.9 | 88 | 63 |
| % recovery ((S + R)/ unprocessed) | | 98% | n/a | n/a | n/a |

A comparison of the results obtained for the CS10 and the SNC are shown in Table 5.

TABLE 5

| Harvest sample | Harvest rate (%) | Viability Improvement (%) | Motility Improvement (%) | Temp Increase (° C.) |
|---|---|---|---|---|
| CS10 | 11.3 | 19 | 14 | 1.7 |
| SNC | 14.9 | 25 | 20 | 0.9 |

As can be seen from Table 5, the SNC results in an increased harvest rate, increased viability and increased motility. One important result observed is that the CS10 has a 1.7° C. temperature increase (even with circulating buffers), while the SNC has only a 0.9° C. increase. This difference is due to the higher sodium chloride concentration in the CS10 buffer which results in a higher electrical current (88 mA). The SNC uses a buffer with a low electrolyte content and, therefore, the current is only 8 mA (only one tenth of the CS10 current). As discussed above, sperm are particularly sensitive to temperature changes and a lower current will protect the biological activity of sperm, such as motility, acrosome integrity, etc.

The SNC makes the separation of viable human sperm easier and faster, without compromising sperm viability. The SNC outperforms the CS10, which is the industry standard.

Example 2—Separation of Platelets

Performance of the sealed non-circulating buffer cartridge (SNC) of the present invention was assessed for the separation of human platelets.

Platelets have an average size about 2-3 μm, which is smaller than most of blood cells such as erythrocytes (4-6 μm) lymphocytes (5-8 μm), leukocytes (10-12 μm), macrophage (15-20 μm).

PVA restriction membranes with a MWCO of 5 kDA and a polycarbonate separation membrane with a pore size of 5 μm were employed in the SNC using the following method:
a) Uncoagulated blood sample was centrifuged at 300 g×20 min.
b) The sample separated into three layers after centrifugation, a bottom layer mainly containing red cells (red layer), a middle layer rich with platelets and leukocytes (buffy coat layer), and a top part layer comprising platelet-rich plasma (plasma layer).
c) The buffy coat and plasma layers were removed to a new tube (referred to as the "original sample").
d) 8 ml of CSM-15 buffer was added into the buffer reservoirs of the SNC.
e) 1200 μl of platelet additive solution (PAS) was added into the sample and harvest chambers simultaneously and left to equilibrate for 5 min.
f) The sample chamber was emptied and 1200 μl of the original sample was added.
g) The SNC was run at a voltage of 25V, a maximum current of 75 mA and a time of 8 minutes.
h) Microscopic assessment was conducted of the original sample, the sample chamber and the harvest chamber.

Figure 7:
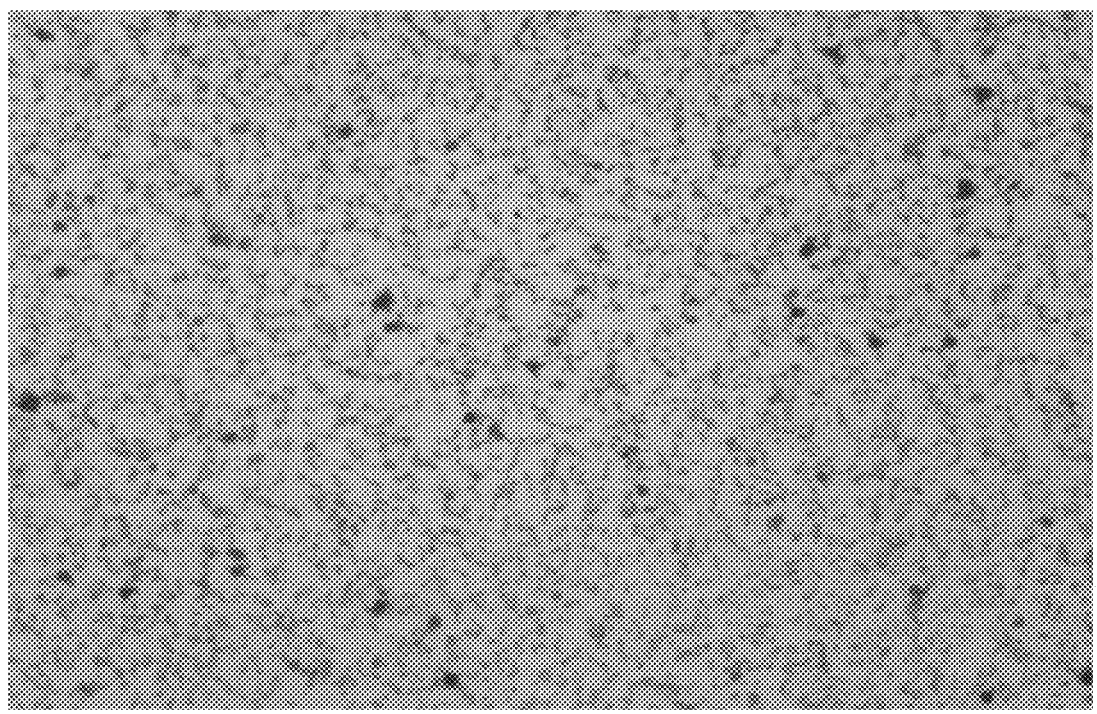
FIG. 7: original sample stained with Haemotoxylin and Eosin stain (HE stained).

The original sample has large quantities of leukocytes, lymphocytes and monocytes—the dark blue cell represents the lymphocyte, the slightly larger pink cells are different types of leukocytes such as eosinophil, basophil, neutrophil (FIG. 7).

Figure 8:
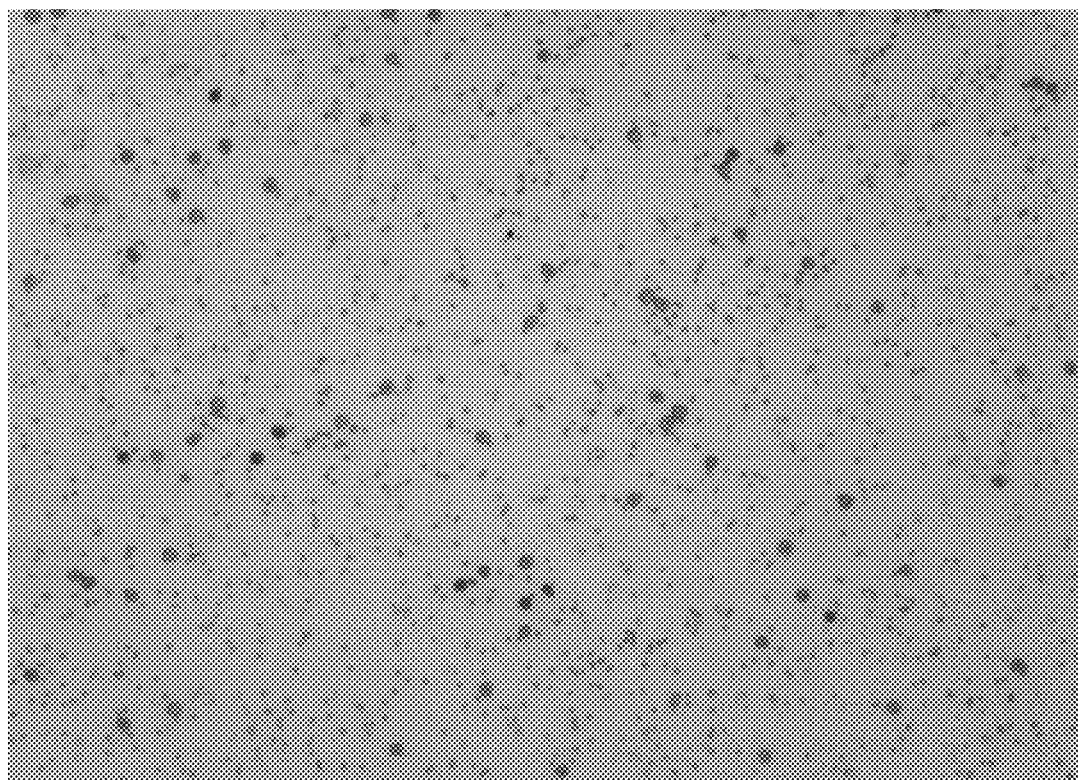
FIG. 8: residual sample from the sample chamber following electrophoresis (HE stained).

The residual sample in the sample chamber was similar to the original sample, but the platelet/leukocytes ratio was reduced significantly because of the movement of most of the platelets into the harvest chamber (FIG. 8). Red cell, platelets and macrophage were observed in residual sample with no cell lysis after 8 min running (FIG. 8).

Figure 9:
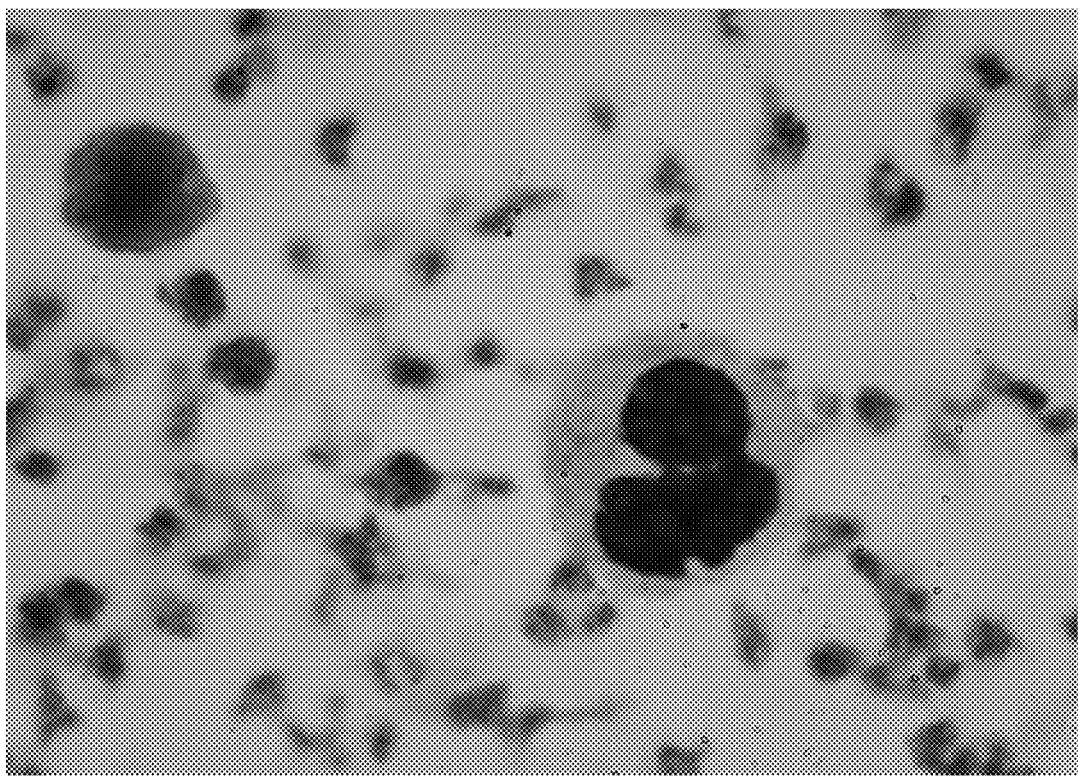
FIG. 9: sample from harvest chamber following electrophoresis (HE stained).

The harvest chamber contained large number of platelets and very few lymphocytes, with almost all the leukocytes and monocytes being removed (FIG. 9).

Figure 10:
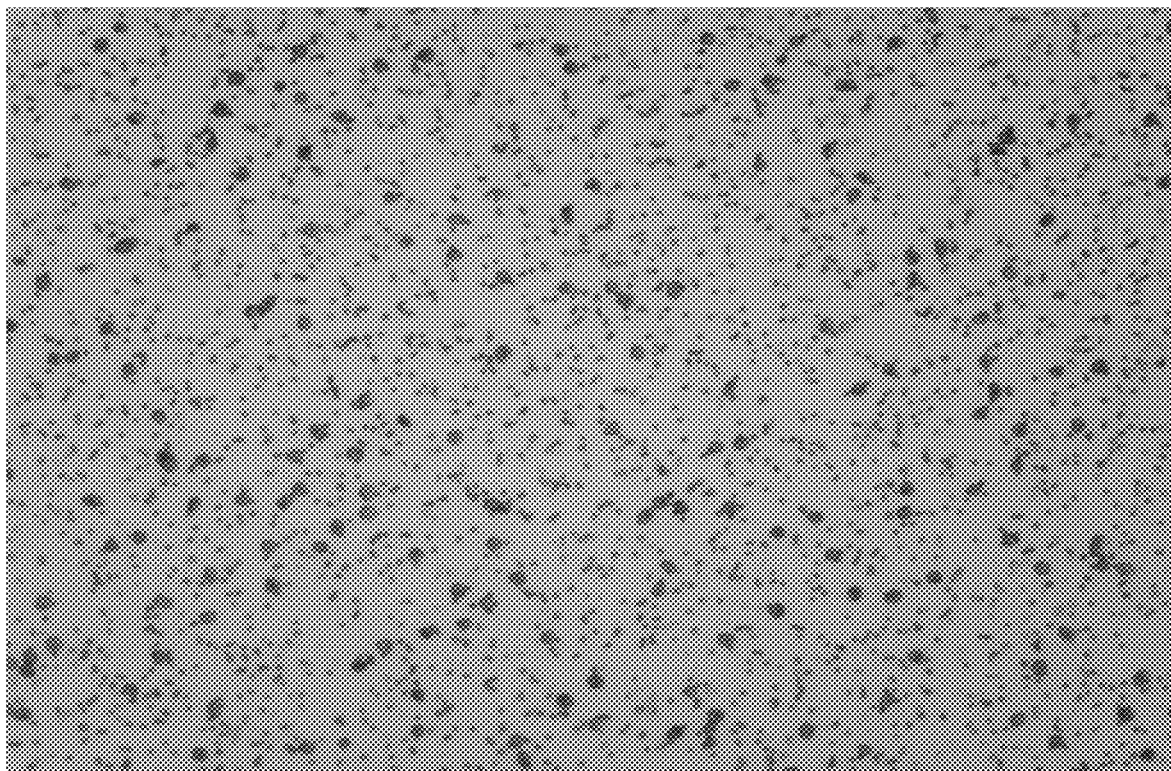
FIG. 10: cells caught on separation membrane following electrophoresis (HE stained).

Large amounts of leukocytes, lymphocytes, monocytes and macrophage were caught on separation membrane (FIG. 10).

The current was monitored throughout the procedure and did not exceed 50 mA (Table 1):

TABLE 6

|  | 0 min | 1 min | 2 min | 3 min | 4 min | 5 min | 6 min | 7 min | 8 min |
|---|---|---|---|---|---|---|---|---|---|
| Voltage (vol) | 0 | 25 | 25 | 25 | 25 | 25 | 25 | 25 | 25 |
| Current (mA) | 0 | 42 | 42 | 42 | 46 | 46 | 50 | 50 | 50 |

The results show that the separation procedure using the SNC is very gentle on cells, allowing the separation of specific cell types without lysis, activation or oxidative damage.

The invention claimed is:

1. An electrophoresis apparatus for separation of cells in a solution, the apparatus comprising:
a sample chamber and a harvest chamber separated by a size-exclusion membrane;
non-circulating buffer chambers flanking each respective sample chamber and harvest chamber, wherein each buffer chamber is separated from each respective sample chamber and harvest chamber by an ion-permeable membrane that does not allow passage of macromolecules or cells, and an electrode positioned in each buffer chamber;
wherein the ion-permeable membranes comprise poly (vinyl alcohol).

2. The apparatus according to claim 1, wherein the non-circulating buffer chambers contain a buffer solution that comprises HEPES.

3. The apparatus according to claim 1, wherein the non-circulating buffer chambers contain a buffer solution that comprises sucrose.

4. The apparatus according to claim 1, wherein the non-circulating buffer chambers contain a buffer solution that comprises 30 mM HEPES and 250 mM sucrose, and has been pH adjusted to 7.8 with Trizma base.

5. The apparatus according to claim 1, wherein each sample chamber and harvest chamber contains an aperture for adding or removing a solution.

6. The apparatus according to claim 5, wherein each aperture is sealable.

7. The apparatus according to claim 1, further comprising a power source, wherein the power source is connected to the electrodes.

8. The apparatus according to claim 1, wherein the apparatus is a cartridge that is insertable into a receiving device comprising a power source such that a voltage may be applied to the electrodes.

9. The apparatus according to claim 8, wherein the cartridge is sterile.

10. A method of using the apparatus according to claim 1 for the separation of cells, the method comprising the steps of: (a) adding a sample comprising the cells to the sample chamber of the apparatus; (b) applying a voltage to the electrodes; and (c) collecting separated cells from the harvest chamber.

11. A method of using the apparatus according to claim 1 for the separation of sperm, the method comprising the steps of: (a) adding a sample comprising the sperm to the sample chamber of the apparatus; (b) applying a voltage to the electrodes; and (c) collecting separated sperm from the harvest chamber.

* * * * *